(12) United States Patent
Taneda

(10) Patent No.: US 9,868,968 B2
(45) Date of Patent: Jan. 16, 2018

(54) METHOD FOR PRODUCING SACCHARIDES CONTAINING GLUCOSE AS MAIN COMPONENT

(71) Applicant: JGC CORPORATION, Tokyo (JP)

(72) Inventor: Daisuke Taneda, Ibaraki (JP)

(73) Assignee: JGC CORPORATION, Tokyo (JP)

( * ) Notice: Subject to any disclaimer, the term of this patent is extended or adjusted under 35 U.S.C. 154(b) by 0 days.

(21) Appl. No.: 15/026,607

(22) PCT Filed: Oct. 4, 2013

(86) PCT No.: PCT/JP2013/077046
§ 371 (c)(1),
(2) Date: Apr. 1, 2016

(87) PCT Pub. No.: WO2015/049785
PCT Pub. Date: Apr. 9, 2015

(65) Prior Publication Data
US 2016/0244794 A1 Aug. 25, 2016

(51) Int. Cl.
*C12P 19/02* (2006.01)
*C12P 19/14* (2006.01)
*C13K 1/02* (2006.01)

(52) U.S. Cl.
CPC .............. *C12P 19/02* (2013.01); *C12P 19/14* (2013.01); *C13K 1/02* (2013.01)

(58) Field of Classification Search
CPC ........................................................ C12P 19/02
See application file for complete search history.

(56) References Cited

U.S. PATENT DOCUMENTS

2008/0138862 A1 6/2008 Felby et al.
2012/0315677 A1* 12/2012 Genta .................. C12P 19/14
435/105

FOREIGN PATENT DOCUMENTS

| JP | 2011-509662 | 3/2011 |
| WO | 2011074479 | 6/2011 |
| WO | 2012095976 | 7/2012 |
| WO | 2013076789 | 5/2013 |

OTHER PUBLICATIONS

United States Sugar Corporation, Molasses Composition, Typical Composition of U.S. Sugar's Heavy Mill Run Cane Molasses, 2003.*
Taneda et al., "Production of High Concentration Sugar Solution by Enzymatic Saccharification," with English translation, SCEJ(Society of Chemical Engineers, Japan) 41st Autumn Meeting, Sep. 16-18, 2009, pp. 146.

(Continued)

*Primary Examiner* — Rosanne Kosson
(74) *Attorney, Agent, or Firm* — JCIPRNET

(57) ABSTRACT

A method for producing saccharides according to the present invention includes a step of preparing a slurry by adding an aqueous solution containing a sugar or a sugar solution to biomass so that the slurry has a biomass content of 10 to 30 w/v %, and a step of adding at least one of an enzyme that degrades cellulose and an enzyme that degrades hemicellulose to the slurry containing the biomass to degrade at least one of cellulose and hemicellulose contained in the biomass, thereby producing saccharides containing glucose as a main component.

4 Claims, 4 Drawing Sheets

(56) References Cited

OTHER PUBLICATIONS

Ueno et al., "Discussion of Enzymatic Saccharification Reaction Mechanism, " with English translation, SCEJ(Society of Chemical Engineers, Japan) 41st Autumn Meeting, Sep. 16-18, 2009, pp. 147.
"International Search Report (Form PCT/ISA/210)", dated Dec. 24, 2013, pp. 1-4, with English translation thereof.

* cited by examiner

METHOD FOR PRODUCING SACCHARIDES CONTAINING GLUCOSE AS MAIN COMPONENT

CROSS-REFERENCE TO RELATED APPLICATION

This application is a 371 application of International PCT application serial no. PCT/JP2013/077046, filed on Oct. 4, 2013. The entirety of each of the above-mentioned patent applications is hereby incorporated by reference herein and made a part of this specification.

TECHNICAL FIELD

The present invention relates to a method for producing saccharides containing glucose as a main component by enzymatically degrading at least one of cellulose and hemicellulose contained in biomass.

BACKGROUND ART

An example of methods for producing bioethanol using cellulose-based biomass as a raw material is an enzymatic ethanol production technique of enzymatically hydrolyzing at least one of cellulose and hemicellulose.

In the case where a solution (hereafter referred to as a "saccharified solution") containing saccharides containing glucose as a main component is produced by enzymatically degrading biomass and then ethanol is produced, a high-concentration saccharified solution with a saccharide concentration of 150 g/L or more needs to be produced. This is because if the saccharide concentration is 150 g/L or less, the concentration of ethanol obtained by fermenting the saccharified solution decreases, and thus a large amount of energy is required when the ethanol is condensed by distillation.

In a known method for producing a high-concentration saccharified solution, however, a large amount of biomass is charged into a reaction vessel and degraded with an enzyme (e.g., refer to PTL 1).

REFERENCE LIST

Patent Literature

PTL 1: U.S. Patent Application Publication No. 2008/0138862

SUMMARY OF INVENTION

Technical Problem

However, if a high-concentration biomass slurry containing a large amount of biomass is charged into a reaction vessel (the concentration of biomass slurry is 30 w/v % or more), the amount of biomass relative to the solution becomes excessively large. Therefore, the solution is absorbed into pores of the biomass (like a sponge having absorbed moisture), and the amount of a solution in a free state decreases. Consequently, the enzyme remains in the pores of the biomass, and free movement of the enzyme between biomass and biomass is restricted.

Furthermore, if the amount of a solution in a free state decreases, the viscosity of the slurry increases. Therefore, when stirring is performed with the same power, the slurry is not sufficiently mixed. This easily causes nonuniform temperature and concentration in the reaction vessel. In particular, when the concentration is not uniform and the sugar concentration is excessively increased locally, the action of the enzyme is considerably inhibited. For these reasons, the degradation efficiency of cellulose and hemicellulose with an enzyme considerably decreases, which poses a problem in that a large amount of enzyme needs to be added. In other words, for the purpose of efficiently saccharifying biomass using an enzyme in an amount as small as possible because an enzyme is expensive, the concentration of the biomass slurry needs to be decreased to 30 w/v % or less. However, when the concentration of the biomass slurry is 30 w/v % or less, the amount of cellulose and hemicellulose serving as raw materials for sugar is small, which poses a problem in that a high-concentration saccharified solution with 150 g/L or more cannot be produced.

SUMMARY OF THE INVENTION

In view of the foregoing, objective of the present invention is to provide a method for producing saccharides containing glucose with high sugar concentration as a main component without using a high-concentration biomass slurry.

Solution to Problem

According to the present invention, a method for producing saccharides containing glucose as a main component includes a step of preparing a slurry by adding an aqueous solution containing a sugar or a sugar solution to biomass so that the slurry has a biomass content of 10 to 30 w/v % and a step of adding at least one of an enzyme that degrades cellulose and an enzyme that degrades hemicellulose to the slurry containing the biomass to degrade at least one of cellulose and hemicellulose contained in the biomass, thereby producing saccharides containing glucose as a main component.

In the method for producing saccharides according to the present invention, in the step of preparing the slurry, when a content of the at least one of cellulose and hemicellulose in the slurry is assumed to be X (w/v %), an initial sugar concentration of the slurry may be lower than a sugar concentration Y (g/L) represented by relation (1) below.

$$Y = -7.7931X + 180 \qquad (1)$$

In the relation (1), $X = W \times C/100$, where W represents a biomass slurry concentration (w/v %) and C represents a proportion (wt %) of the cellulose and the hemicellulose contained in the biomass.

In the method for producing saccharides according to the present invention, the sugar may be glucose or sucrose.

In the method for producing saccharides according to the present invention, the sugar solution may be an enzymatically saccharified solution or a solution containing a sugarcane juice.

In the method for producing saccharides according to the present invention, an adsorption inhibitor for preventing adsorption of an enzyme onto lignin contained in the biomass may be added to the slurry.

Advantageous Effects of Invention

According to the present invention, when a slurry containing biomass is prepared, an aqueous solution containing a sugar or a sugar solution is added to the biomass in advance. Therefore, the action of an enzyme is inhibited by sugar, and thus the activity of the enzyme is reduced compared with the case where the aqueous solution containing a sugar or a sugar solution is not added. However, the biomass content in the slurry containing the biomass can be decreased to 10 to 30 w/v %, while still producing high-concentration saccharified solution. Since the amount of a solution in a free state relative to solid matter is large, the enzyme can freely move in the biomass slurry and the slurry is easily stirred. Consequently, the temperature and concentration in a reaction vessel can be uniformly maintained, which can improve the reactivity between the enzyme and at least one of cellulose and hemicellulose. In other words, when an aqueous solution containing a sugar or a sugar solution is added to biomass in advance, a negative influence and a positive influence are generated in an enzymatic saccharification reaction. However, the positive influence is stronger than the negative influence when the concentration of a sugar added is set to an appropriate value. As a result, a high-concentration saccharified solution with 150 g/L or more can be efficiently produced using a small amount of enzyme.

DETAILED DESCRIPTION OF THE INVENTION

Figure 1:
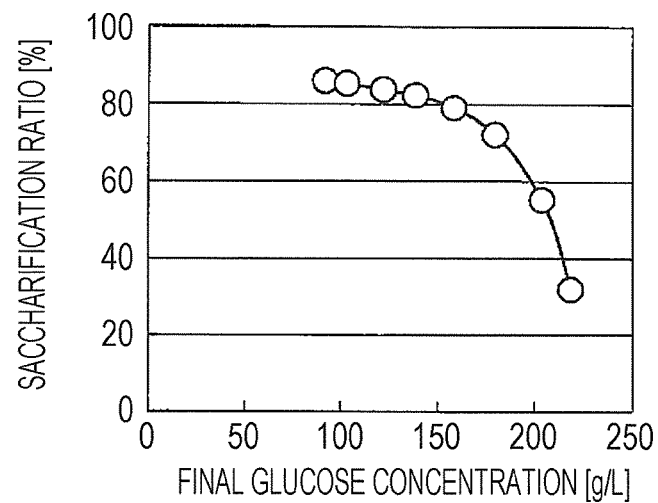
FIG. 1 is a graph illustrating the relationship between the saccharification ratio obtained when glucose solutions having different concentrations are added at the initial stage and enzymatic saccharification of steam-exploded bagasse is performed and the final glucose concentration after the saccharification is completed.

Methods for producing saccharides according to embodiments of the present invention will be described.

These embodiments are specifically described for facilitating the understanding of the gist of the invention and do not limit the present invention unless otherwise specified.

The method for producing saccharides according to this embodiment is a method including a step of preparing a slurry by adding an aqueous solution containing a sugar or a sugar solution to biomass so that the slurry has a biomass content of 10 to 30 w/v % and a step of adding at least one of an enzyme that degrades cellulose and an enzyme that degrades hemicellulose to the slurry containing the biomass to degrade at least one of cellulose and hemicellulose contained in the biomass, thereby producing saccharides containing glucose as a main component.

In the method for producing saccharides containing glucose as a main component according to this embodiment, first, biomass (wood, grass, or agricultural residues) is subjected to a pretreatment for improving the contact efficiency between at least one of cellulose and hemicellulose contained in the biomass and at least one of an enzyme that degrades cellulose and an enzyme that degrades hemicellulose.

Examples of the pretreatment include an alkali treatment, an organic solvent treatment, a dilute sulfuric acid treatment, a steam explosion treatment for the biomass. From the viewpoint of enzymatic saccharification yield and facility cost, a steam explosion treatment, an alkali treatment, or a dilute sulfuric acid treatment is suitably employed.

A publicly known treatment is employed for the alkali treatment, organic solvent treatment, dilute sulfuric acid treatment, or steam explosion treatment for the biomass.

Subsequently, a slurry (hereafter may also be referred to as "biomass slurry") containing the pretreated biomass is prepared.

The concentration of the biomass slurry, that is, the biomass content in the biomass slurry is appropriately controlled in accordance with the type of biomass, the pretreatment method, or the like, and is preferably 10 g to 30 g relative to 100 mL of a solution, namely, 10 w/v % to 30 w/v %.

When the biomass content in the biomass slurry is within the above range, the entire solution is not absorbed into pores of the biomass, and a certain amount of the solution is present in a free state. Therefore, an enzyme can freely move in the biomass slurry. Furthermore, the stirring operation of the biomass slurry is easily performed, and thus the reactivity between the enzyme and at least one of cellulose and hemicellulose improves. If the concentration of the biomass slurry is less than 10 w/v %, the production efficiency of saccharides containing glucose as a main component is unfavorably low.

When the slurry containing the biomass is prepared, an aqueous solution containing a sugar or a sugar solution is added to the biomass.

In the case where the slurry is prepared by adding an aqueous solution containing a sugar or a sugar solution to the biomass, when the content of at least one of cellulose and hemicellulose of the biomass in the slurry is assumed to be X (w/v %), the initial sugar concentration of the slurry is preferably lower than the sugar concentration Y (g/L) represented by relation (1) below.

$$Y = -7.7931X + 180 \quad (1)$$

In the above relation, $X = W \times C/100$, where W represents a biomass slurry concentration (w/v %) and C represents a proportion (wt %) of the cellulose and the hemicellulose contained in the biomass.

After at least one of the cellulose and the hemicellulose is degraded with at least one of the enzyme that degrades cellulose and the enzyme that degrades hemicellulose (after enzymatic saccharification), it is ideal to collect a solution with a maximum sugar concentration. In reality, however, when the sugar concentration increases, the action of at least one of the enzyme that degrades cellulose and the enzyme that degrades hemicellulose is inhibited by sugar, which decreases the activity of the enzyme.

Thus, the relationship between the concentration of glucose (final glucose concentration) obtained by enzymatic saccharification of at least one of cellulose and hemicellulose and the saccharification ratio of biomass was investigated by the following method to determine the final glucose concentration at which at least one of the enzyme that degrades cellulose and the enzyme that degrades hemicellulose is inhibited.

A slurry containing biomass (biomass slurry) was prepared by dispersing 10 g-dry of steam-exploded bagasse (hereafter referred to as "biomass") in 50 mL of water or 50 mL of a glucose-containing aqueous solution.

In the preparation of the biomass slurry, the concentration of glucose contained in the biomass slurry was changed in the range of 0 to 185 g/L. The concentration of glucose contained in the biomass slurry at the time of the preparation of the biomass slurry is defined as an initial glucose concentration.

Subsequently, cellulose and hemicellulose contained in the biomass slurry were degraded using cellulase under the following conditions.

Weight of biomass: 10 g-dry

Amount of cellulase added: 4 mg/g-substrate

Initial glucose concentration: 0 to 185 g/L

Amount of glucose-containing aqueous solution: 50 mL

Temperature: 50° C.

pH: 5

The results are shown in Table 1 and FIG. 1.

TABLE 1

| Final glucose concentration (g/L) | Saccharification ratio (%) | Initial glucose concentration (g/L) |
| --- | --- | --- |
| 92 | 86 | 0 |
| 103 | 85 | 15 |
| 122 | 83.5 | 35 |
| 138 | 82 | 50 |
| 158 | 79 | 75 |
| 179 | 72 | 105 |
| 203 | 55 | 145 |
| 218 | 32 | 185 |

As is clear from the results shown in Table 1 and FIG. 1, when the final glucose concentration exceeds 180 g/L, the saccharification ratio sharply decreases. In other words, the glucose concentration (maximum permissible glucose concentration) at which the inhibition of at least one of the enzyme that degrades cellulose and the enzyme that degrades hemicellulose can be permitted is 180 g/L.

Furthermore, the cellulose and the hemicellulose contained in the biomass slurry were degraded using cellulase by performing the same experiment as above, except that the biomass slurry was prepared using steam-exploded bagasse as biomass and using sucrose instead of the glucose. The results are shown in Table 2 and FIG. 2.

TABLE 2

| Final total concentration of glucose and sucrose (g/L) | Saccharification ratio (%) | Initial glucose concentration (g/L) |
| --- | --- | --- |
| 92 | 86 | 0 |
| 104 | 84 | 15 |
| 122 | 82 | 35 |
| 136 | 81.5 | 50 |
| 158 | 78 | 75 |
| 181 | 72 | 105 |
| 202 | 54 | 145 |
| 218 | 31 | 185 |

Figure 2:
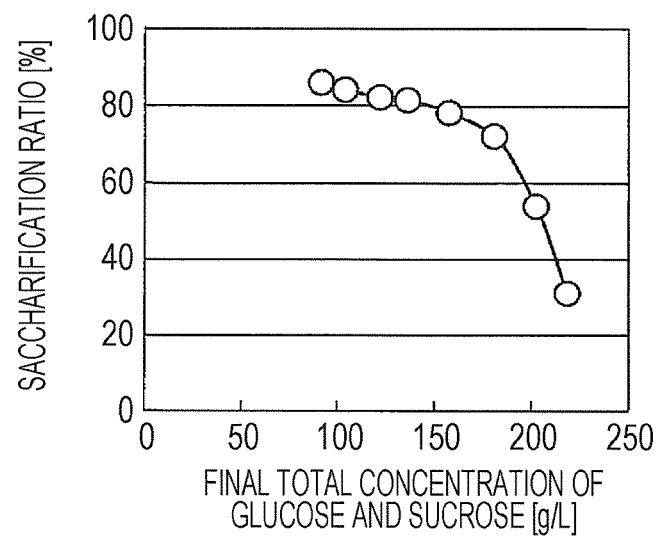
FIG. 2 is a graph illustrating the relationship between the saccharification ratio obtained when sucrose solutions having different concentrations are added at the initial stage and enzymatic saccharification of steam-exploded bagasse is performed and the total concentration of the final glucose concentration and the final sucrose concentration after the saccharification is completed.

As is clear from the results shown in Table 2 and FIG. 2, the relationship between the final total concentration of glucose and sucrose after the enzymatic saccharification, the saccharification ratio, and the initial sucrose concentration is substantially the same as that in Table 1 and FIG. 1. In other words, the sugar concentration (maximum permissible sugar concentration) at which the inhibition of at least one of the enzyme that degrades cellulose and the enzyme that degrades hemicellulose can be permitted is also 180 g/L in the case of a mixed sugar of glucose and sucrose.

It has been found from the above results that when a slurry containing biomass is prepared by adding an aqueous solution containing glucose or sucrose to biomass and enzymatic saccharification is performed, the upper limit of the concentration (initial glucose concentration) of glucose contained in the slurry or the concentration (initial sucrose concentration) of sucrose contained in the slurry needs to be within a range in which the final glucose concentration or the final total concentration of the glucose and sucrose after the slurry is enzymatically saccharified is less than 180 g/L.

Subsequently, the initially-added-glucose concentration and the initially-added-sucrose concentration required for satisfying that the final glucose concentration or the final total concentration of glucose and sucrose after the enzymatic saccharification was 180 g/L were investigated.

The initial glucose concentration or the initial sucrose concentration required for satisfying that the final glucose concentration or the final total concentration of glucose and sucrose was 180 g/L was determined using the following method by changing the type of biomass and the concentration of biomass in the slurry containing the biomass.

Steam-exploded bagasse or eucalyptus was dispersed in 50 mL of a glucose-containing aqueous solution to prepare a glucose-containing slurry that contains bagasse or eucalyptus. Furthermore, steam-exploded bagasse was dispersed in 50 mL of a sucrose-containing aqueous solution to prepare a sucrose-containing slurry that contains bagasse.

In the preparation of the slurry, the concentration of glucose or sucrose contained in the slurry was changed in the range of 40 to 172 g/L. The concentration of glucose or sucrose contained in the slurry at the time of the preparation of the slurry is defined as an initial glucose concentration or an initial sucrose concentration.

Subsequently, the bagasse or eucalyptus contained in the slurry was degraded using cellulase under the following conditions.

Biomass concentration in slurry containing biomass: 2, 5, 10, 15, 20, 25, 30, 32, and 37 w/v %

Amount of cellulase added: 4 mg/g-substrate

Initial glucose concentration or initial sucrose concentration: 40 to 172 g/L

Amount of glucose-containing aqueous solution or sucrose-containing aqueous solution: 50 mL Temperature: 50° C.

pH: 5

The content of the cellulose and hemicellulose contained in the steam-exploded bagasse was 52%. The content of the cellulose and hemicellulose contained in the steam-exploded eucalyptus was 60%. As a result, the content of the cellulose and hemicellulose contained in the slurry containing biomass was in the range of 1.2 to 19.2 w/v %.

Figure 3:
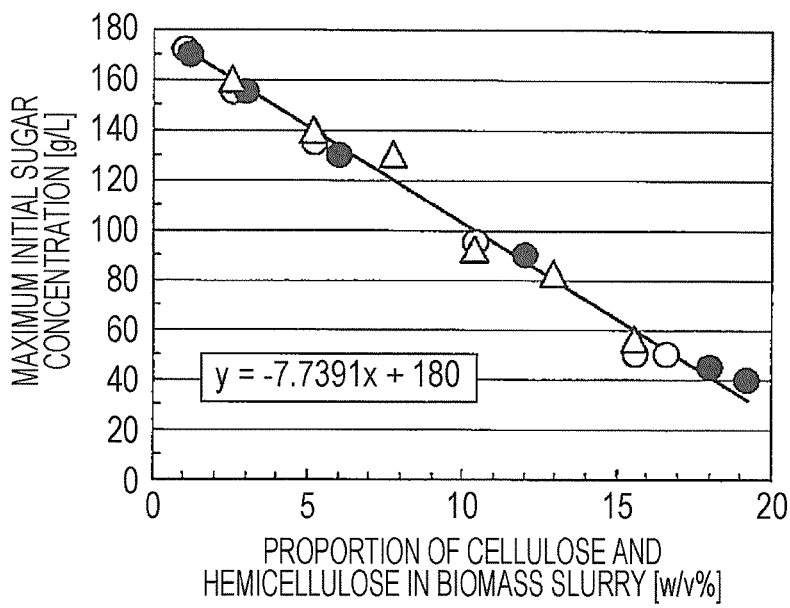
FIG. 3 is a graph illustrating the relationship between the initial glucose concentration or the initial sucrose concentration required to satisfy the sugar concentration of 180 g/L after the enzymatic saccharification and the concentration of cellulose and hemicellulose contained in a slurry containing biomass.

The results are shown in FIG. 3.

In FIG. 3, "○ (solid-white circle)" refers to a case where the steam-exploded bagasse was dispersed in the glucose-containing aqueous solution, "Δ (solid-white triangle)" refers to a case where the steam-exploded bagasse was dispersed in the sucrose-containing aqueous solution, and "● (solid-black circle)" refers to a case where the steam-exploded eucalyptus was dispersed in the glucose-containing aqueous solution.

FIG. 3 is a graph illustrating the relationship between the initial glucose concentration or the initial sucrose concentration required for satisfying that the sugar concentration (the glucose concentration or the total concentration of glucose and sucrose) after the enzymatic saccharification is 180 g/L and the concentration (w/v %) of cellulose and hemicellulose contained in the slurry containing the biomass.

The above relation (1) is obtained by approximating the results in FIG. 3 with a linear expression.

In this relation, X represents the content of cellulose and hemicellulose of biomass contained in the slurry containing the biomass; Y represents the initial glucose concentration or the initial sucrose concentration in the slurry containing the biomass, the concentration being required for satisfying that the sugar concentration is 180 g/L after the enzymatic saccharification; W represents the biomass slurry concentration (w/v %); C represents the proportion (wt %) of the cellulose and hemicellulose contained in the biomass; and X is defined as $X = W \times C/100$.

An example of the solution (solvent) used for the biomass slurry is water.

In the preparation of the biomass slurry, the sugar added to the biomass is, for example, glucose or sucrose.

In the preparation of the biomass slurry, the sugar solution added to the biomass is preferably an enzymatically saccharified solution or a solution containing a sugarcane juice. Examples of the saccharide contained in this solution include glucose, xylose, and sucrose.

The enzymatically saccharified solution is a high-concentration sugar solution produced in advance by the method for producing saccharides containing glucose as a main component according to this embodiment.

An adsorption inhibitor is preferably added to the biomass slurry in order to prevent an enzyme (at least one of an enzyme that degrades cellulose and an enzyme that degrades hemicellulose) from being adsorbed onto lignin contained in the biomass (enzymatic adsorption).

In the case where the method for producing saccharides containing glucose as a main component according to this embodiment is combined with a method for producing saccharides from sugarcane or grain such as corn, that is, in the case where the production of saccharides from sugarcane or grain such as corn is combined with the production of saccharides from residues (biomass) of such agricultural products, when the biomass slurry is prepared, the sugar added to the biomass slurry is, for example, a saccharide produced from sugarcane or grain such as corn.

In the case where the method for producing saccharides containing glucose as a main component according to this embodiment is used alone, the sugar solution added to the biomass slurry is a sugar solution obtained by recycling a part of saccharides produced by the method for producing saccharides containing glucose as a main component according to this embodiment.

In the case where the relationship between X and Y is represented by the above relation (1) ($X = W \times C/100$) and the slurry containing biomass is prepared by adding a sugar or a sugar solution to the biomass, the initial sugar concentration in the biomass slurry is preferably a sugar concentration lower than Y. When the initial sugar concentration in the biomass slurry is within the above range, the influence of reaction inhibition due to the saccharides added is suppressed during the hydrolysis of the biomass with an enzyme, which allows efficient production of a saccharified solution with a sugar concentration of 150 g/L or more.

Subsequently, the biomass slurry and an aqueous solution (enzyme aqueous solution) containing an appropriate amount of cellulase, which is suitable for the degradation of at least one of cellulose and hemicellulose contained in the biomass slurry, are added to mix the biomass slurry and the enzyme aqueous solution (preparation step).

In this preparation step, the pH of the reaction vessel solution containing the biomass slurry and the enzyme aqueous solution is adjusted so that the pH condition of the reaction vessel solution is optimum for the enzyme used. Furthermore, the temperature of the reaction vessel is adjusted so that temperature conditions are optimum for the enzyme used.

In this preparation step, the pH of a mixture containing the biomass slurry, the enzyme aqueous solution, and additives is preferably adjusted so that the enzyme actively works. Specifically, the pH of the reaction-system aqueous solution is preferably adjusted to 4 to 6.

In this preparation step, the temperature of the mixture is preferably adjusted so that the enzyme actively works. Specifically, the temperature of the reaction system is preferably increased to 40° C. to 60° C.

Cellulase is used as an enzyme for degrading the biomass.

If a large amount of hemicellulose is contained in the biomass, xylanase or mannanase is preferably added as an enzyme for degrading hemicellulose, in addition to the cellulase.

The mixture is stirred with a stirring blade or the like.

In this embodiment, the mixture is mixed by being gently stirred in the reaction vessel to the degree that the enzyme contained in the enzyme aqueous solution is not excessively deactivated. Thus, the biomass (at least one of cellulose and hemicellulose) is efficiently enzymatically saccharified (enzymatic saccharification reaction step).

In this enzymatic saccharification reaction step, the temperature of the mixture is preferably adjusted so that the enzyme actively works. Specifically, the temperature of the mixture is preferably kept at 40° C. to 60° C.

The enzymatic saccharification reaction step is performed until the saccharification of the biomass due to the enzyme sufficiently proceeds and the reaction will no longer proceed. For example, the biomass is enzymatically degraded at 40° C. to 60° C. for about 2 to 20 days.

In the method for producing saccharides containing glucose as a main component according to this embodiment, an additive for suppressing the adsorption of an enzyme onto lignin is preferably added to the biomass slurry or the mixture containing the biomass slurry and the enzyme aqueous solution.

When saccharides containing glucose as a main component are produced by enzymatically degrading at least one of cellulose and hemicellulose contained in the biomass, a part of the enzyme added adsorbs onto lignin, which is one of components constituting the biomass. The enzyme that has adsorbed onto the lignin does not easily desorb from the lignin. Therefore, it is known that such an enzyme does not have a function of hydrolyzing at least one of cellulose and hemicellulose to produce saccharides. Such a phenomenon is called "unproductive adsorption of enzyme onto lignin". The prevention of this unproductive adsorption leads to a reduction in the amount of an enzyme used.

Examples of the additive for preventing the unproductive adsorption onto lignin include bovine serum albumin (BSA), cheese whey, and proteins derived from grain.

In the method for producing saccharides containing glucose as a main component according to this embodiment, the content of at least one of cellulose and hemicellulose of biomass in the slurry containing the biomass is 10 to 30 w/v % and an aqueous solution containing a sugar or a sugar solution is added to the biomass in the preparation of the slurry containing the biomass. When the content of at least one of cellulose and hemicellulose of the biomass contained in the slurry is assumed to be X (w/v %), the addition amount of the aqueous solution containing a sugar or a sugar solution is set so that the initial sugar concentration of the slurry is lower than the sugar concentration Y (g/L) represented by the above relation (1). As a result, a high-concentration saccharified solution with 150 g/L or more can be collected while the biomass concentration in the biomass slurry is set to be a low value (10 to 30 w/v %). Furthermore, the content of at least one of cellulose and hemicellulose of the biomass contained in the biomass slurry can be set to a low value (10 to 30 w/v %), which increases the proportion of free water in the biomass slurry. If such free water is sufficiently present, the enzyme can freely move in the biomass slurry and the viscosity of the slurry can be kept low. Therefore, stirring is easily performed and the temperature and concentration distribution in the reaction vessel can be made uniform. This improves the reactivity between the enzyme and at least one of cellulose and hemicellulose and thus decreases the amount of an enzyme used. In a known method in which the content of at least one of cellulose and hemicellulose of the biomass contained in the biomass slurry is set to 10 to 30 w/v % without adding the aqueous solution containing a sugar or a sugar solution to the biomass, the free water is sufficiently present, but the biomass content is low, which poses a problem in that the concentration of the sugar solution to be obtained decreases. Furthermore, if the content of at least one of cellulose and hemicellulose of the biomass contained in the biomass slurry is set to 30 w/v % or more in order to produce a high-concentration saccharified solution with 150 g/L or more, most of the solution is absorbed into the biomass. Consequently, the amount of free water decreases and thus the enzyme cannot freely move. This decreases the reactivity between the enzyme and at least one of cellulose and hemicellulose, and increases the amount of an enzyme required. In view of the foregoing, by adding a sugar or a sugar solution to biomass slurry in advance while suppressing the content of at least one of cellulose and hemicellulose of biomass contained in the biomass slurry to be 10 to 30 w/v %, a high-concentration saccharified solution with a saccharide concentration of 150 g/L or more can be produced using a small amount of enzyme. Use of the thus-obtained high-concentration saccharified solution not only downsizes the facilities for ethanol production processes and other biorefinery processes, but also decreases the amount of utility.

Furthermore, when a sugarcane ethanol plant and a cellulose-based ethanol plant are established in combination, the concentration of the sugar solution produced in the cellulose-based ethanol plant needs to be substantially equal to the concentration of the sugar solution squeezed in the sugarcane ethanol plant. Therefore, the method for producing saccharides containing glucose as a main component according to this embodiment is essential.

In a known method for producing a high-concentration saccharified solution, basically, a high-concentration biomass slurry is prepared and the biomass slurry is enzymatically saccharified. In this production method, the efficiency of the enzymatic saccharification is poor. Therefore, the research and development has been aimed at improving a pretreatment method for biomass and producing a high-activity enzyme.

Furthermore, the addition of saccharides such as glucose to a biomass slurry during enzymatic saccharification has been believed to be an absurd idea because an enzymatic saccharification reaction is inhibited by saccharides such as glucose. However, the present inventors have found that when a high-concentration saccharified solution with a saccharide concentration of 150 g/L or more is produced, the amount of an enzyme used can be decreased in the case where the biomass content in a biomass slurry is controlled to be in an appropriate range (10 w/v % to 30 w/v %) and a sugar or a sugar solution is added to the biomass slurry, compared with the case where the biomass content in a biomass slurry is increased (30 w/v % or more) and the amount of an enzyme added is increased. This is because a reaction promoting effect achieved by suppressing the concentration of the biomass slurry to be 10 to 30 w/v % is larger than a reaction inhibiting effect produced when a sugar such as glucose is added.

When the method for producing saccharides containing glucose as a main component according to this embodiment is employed, the appropriate plant is an ethanol production plant including, in combination, a plant at which ethanol is produced from sugarcane or grain such as corn and a plant to which this production method is applied.

EXAMPLES

Hereafter, the present invention will be further specifically described based on Examples, Comparative Examples, and Experimental Examples. The present invention is not limited to Examples and Experimental Examples below.

Example 1

A slurry containing bagasse was prepared by dispersing 10 g of steam-exploded bagasse in 50 mL of water. The content of the bagasse in the prepared slurry was 20 w/v %.

Subsequently, glucose was added to the slurry so that the concentration of the glucose in the biomass slurry was 60 g/L.

Then, the bagasse contained in the biomass slurry was degraded using cellulase under the following conditions.
Weight of bagasse: 10 g-dry
Amount of cellulase added: 2 mg/g-substrate
Amount of solution: 50 mL
Temperature: 50° C.
pH: 5

Figure 4:
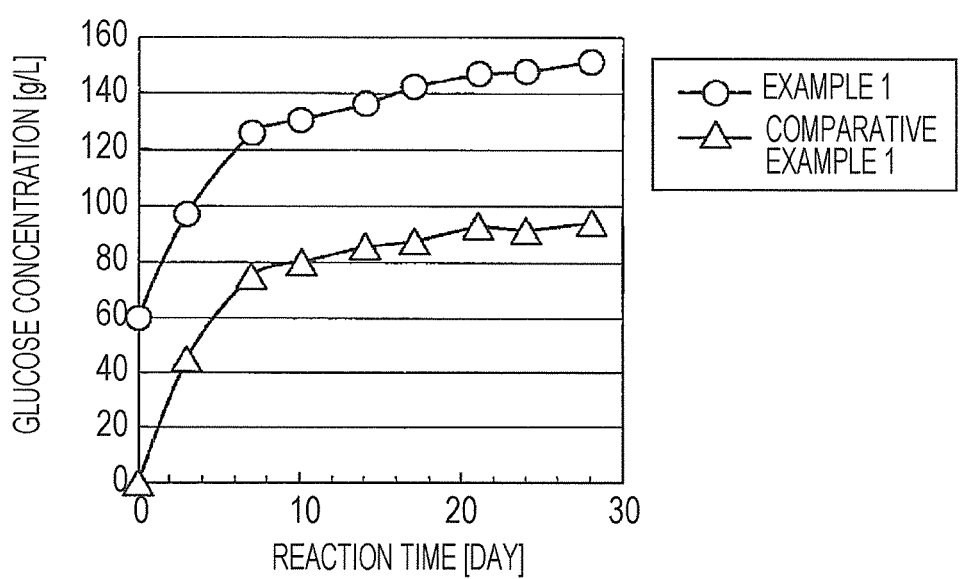
FIG. 4 is a graph illustrating the relationship between the reaction time of enzymatic degradation and the concentration of glucose produced in Example 1 and Comparative Example 1.

The relationship between the enzyme degradation reaction time (day) and the concentration (g/L) of the glucose in the solution was investigated. The results are shown in FIG. 4.

Comparative Example 1

The bagasse contained in the biomass slurry was degraded using cellulase in the same manner as in Example 1, except that the glucose was not added to the biomass slurry.

The relationship between the enzyme degradation reaction time (day) and the concentration (g/L) of the glucose in the solution was investigated. The results are shown in FIG. 4.

It was found from the results in FIG. 4 that the concentration of glucose obtained by enzymatic degradation was considerably improved in Example 1 in which glucose was added to the biomass slurry compared with Comparative Example 1 in which glucose was not added to the biomass slurry. Specifically, the concentration of glucose in the solution was 90 g/L in Comparative Example 1 whereas the concentration of glucose in the solution was 150 g/L in Example 1.

Example 2

A slurry containing rice straw was prepared by dispersing 10 g of steam-exploded rice straw in 50 mL of water. The content of the bagasse in the prepared slurry was 20 w/v %.

Subsequently, glucose was added to the slurry so that the concentration of the glucose in the biomass slurry was 70 g/L.

Then, the rice straw contained in the biomass slurry was degraded using cellulase under the following conditions.
Weight of rice straw: 10 g-dry
Amount of cellulase added: 7 mg/g-substrate
Amount of solution: 50 mL
Temperature: 50° C.
pH: 5

Figure 5:
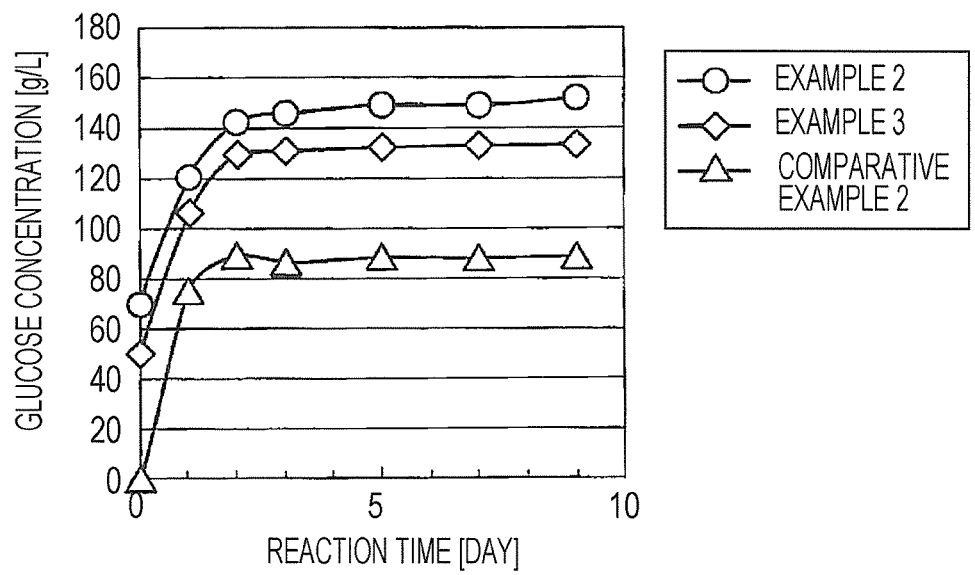
FIG. 5 is a graph illustrating the relationship between the reaction time of enzymatic degradation and the concentration of glucose produced in Examples 2 and 3 and Comparative Example 2.

The relationship between the enzyme degradation reaction time (day) and the concentration (g/L) of the glucose in the solution was investigated. The results are shown in FIG. 5.

Example 3

The rice straw contained in the biomass slurry was degraded using cellulase in the same manner as in Example 2, except that the concentration of glucose in the biomass slurry was changed to 50 g/L.

The relationship between the enzyme degradation reaction time (day) and the concentration (g/L) of the glucose in the solution was investigated. The results are shown in FIG. 5.

Comparative Example 2

The rice straw contained in the biomass slurry was degraded using cellulase in the same manner as in Example 2, except that the glucose was not added to the biomass slurry.

The relationship between the enzyme degradation reaction time (day) and the concentration (g/L) of the glucose in the solution was investigated. The results are shown in FIG. 5.

It was found from the results in FIG. 5 that the concentration of glucose obtained by enzymatic degradation was considerably improved in Examples 2 and 3 in which glucose was added to the biomass slurry compared with Comparative Example 2 in which glucose was not added to the biomass slurry. Specifically, the concentration of glucose in the solution was 90 g/L in Comparative Example 2 whereas the concentration of glucose in the solution was 150 g/L in Example 2 and the concentration of glucose in the solution was 135 g/L in Example 3.

Example 4

A slurry containing bagasse was prepared by dispersing 10 g of steam-exploded bagasse in 50 mL of water. The content of the bagasse in the prepared slurry was 20 w/v %.

Subsequently, a sugarcane juice (sucrose) was added to the slurry so that the concentration of the sugarcane juice in the biomass slurry was 66 g/L.

Then, the bagasse contained in the biomass slurry was degraded using cellulase under the following conditions.
Weight of bagasse: 10 g-dry
Amount of cellulase added: 2 mg/g-substrate
Amount of solution: 50 mL
Temperature: 50° C.
pH: 5

Figure 6:
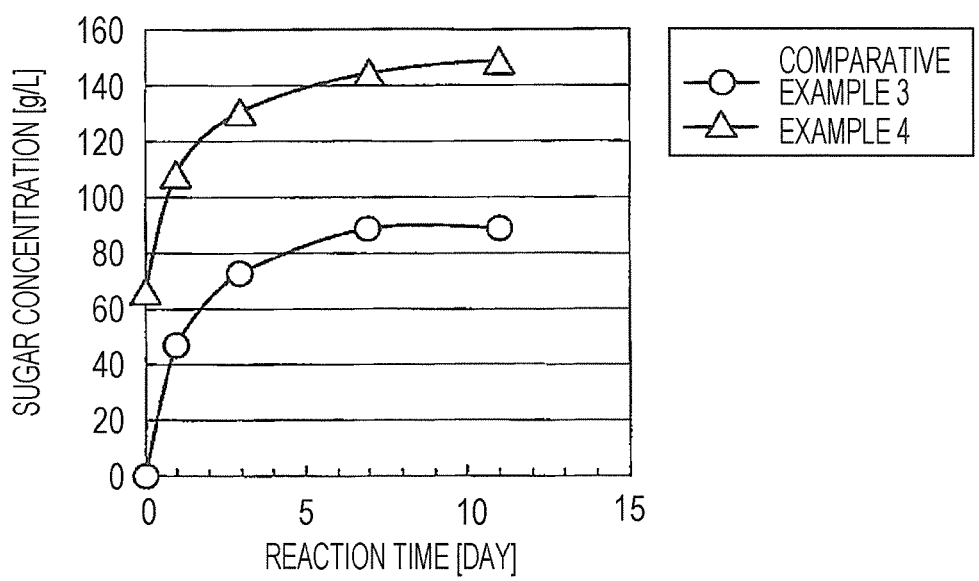
FIG. 6 is a graph illustrating the relationship between the reaction time of enzymatic degradation and the concentration of glucose produced in Example 4 and Comparative Example 3.

The relationship between the enzyme degradation reaction time (day) and the total concentration (g/L) of the glucose and sucrose in the solution was investigated. The results are shown in FIG. 6.

Comparative Example 3

The bagasse contained in the biomass slurry was degraded using cellulase in the same manner as in Example 4, except that the sugarcane juice was not added to the biomass slurry.

The relationship between the enzyme degradation reaction time (day) and the total concentration (g/L) of the glucose and sucrose in the solution was investigated. The results are shown in FIG. 6.

It was found from the results in FIG. 6 that the concentration of glucose obtained by enzymatic degradation was considerably improved in Example 4 in which a sugarcane juice was added to the biomass slurry compared with Comparative Example 3 in which glucose was not added to the biomass slurry. Specifically, the concentration of glucose in the solution was 90 g/L in Comparative Example 3 whereas the total concentration of glucose and sucrose in the solution was 150 g/L in Example 4.

Experimental Example 1

A slurry containing bagasse was prepared by dispersing 1 g-dry of steam-exploded bagasse in 50 mL of a glucose-containing aqueous solution. The content (biomass slurry concentration) of the bagasse in the prepared slurry was 2 w/v %. The concentration (initial glucose concentration) of glucose contained in the slurry was adjusted to 140 g/L.

Subsequently, the bagasse contained in the biomass slurry was degraded using cellulase under the following conditions.
Weight of bagasse: 1 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The saccharification ratio of bagasse was assumed to be 100% when the entire cellulose contained in the bagasse was degraded into glucose. The saccharification ratio of cellulose was calculated from the amount of glucose produced.

Figure 7:
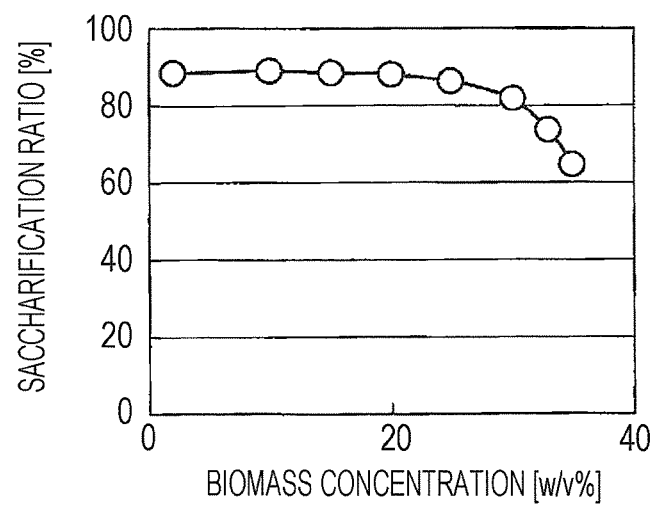
FIG. 7 is a graph illustrating the relationship between the saccharification ratio of biomass and the biomass concentration in Experimental Examples 1 to 8.

The results are shown in Table 3 and FIG. 7.

Experimental Example 2

A slurry containing bagasse was prepared by dispersing 5 g-dry of steam-exploded bagasse in 50 mL of a glucose-containing aqueous solution. The content (biomass slurry concentration) of the bagasse in the prepared slurry was 10 w/v %. The concentration (initial glucose concentration) of glucose contained in the slurry was adjusted to 105 g/L.

Subsequently, the bagasse contained in the biomass slurry was degraded using cellulase under the following conditions.
Weight of bagasse: 5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 3

A slurry containing bagasse was prepared by dispersing 7.5 g-dry of steam-exploded bagasse in 50 mL of a glucose-containing aqueous solution. The content (biomass slurry concentration) of the bagasse in the prepared slurry was 15 w/v %. The concentration (initial glucose concentration) of glucose contained in the slurry was adjusted to 80 g/L.

Subsequently, the bagasse contained in the biomass slurry was degraded using cellulase under the following conditions.
Weight of bagasse: 7.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 4

A slurry containing bagasse was prepared by dispersing 10 g-dry of steam-exploded bagasse in 50 mL of a glucose-containing aqueous solution. The content (biomass slurry concentration) of the bagasse in the prepared slurry was 20 w/v %. The concentration (initial glucose concentration) of glucose contained in the slurry was adjusted to 60 g/L.

Subsequently, the bagasse contained in the biomass slurry was degraded using cellulase under the following conditions.
Weight of bagasse: 10 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 5

A slurry containing bagasse was prepared by dispersing 12.5 g-dry of steam-exploded bagasse in 50 mL of a glucose-containing aqueous solution. The content (biomass slurry concentration) of the bagasse in the prepared slurry was 25 w/v %. The concentration (initial glucose concentration) of glucose contained in the slurry was adjusted to 40 g/L.

Subsequently, the bagasse contained in the biomass slurry was degraded using cellulase under the following conditions.
Weight of bagasse: 12.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 6

A slurry containing bagasse was prepared by dispersing 15 g-dry of steam-exploded bagasse in 50 mL of a glucose-containing aqueous solution. The content (biomass slurry concentration) of the bagasse in the prepared slurry was 30 w/v %. The concentration (initial glucose concentration) of glucose contained in the slurry was adjusted to 25 g/L.

Subsequently, the bagasse contained in the biomass slurry was degraded using cellulase under the following conditions.
Weight of bagasse: 15 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 7

A slurry containing bagasse was prepared by dispersing 16.5 g-dry of steam-exploded bagasse in 50 mL of a glucose-containing aqueous solution. The content (biomass slurry concentration) of the bagasse in the prepared slurry was 33 w/v %. The concentration (initial glucose concentration) of glucose contained in the slurry was adjusted to 25 g/L.

Subsequently, the bagasse contained in the biomass slurry was degraded using cellulase under the following conditions.
Weight of bagasse: 16.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

Experimental Example 8

A slurry containing bagasse was prepared by dispersing 17.5 g-dry of steam-exploded bagasse in 50 mL of a glucose-containing aqueous solution. The content (biomass slurry concentration) of the bagasse in the prepared slurry was 35 w/v %. The concentration (initial glucose concentration) of glucose contained in the slurry was adjusted to 30 g/L.

Subsequently, the bagasse contained in the biomass slurry was degraded using cellulase under the following conditions.
Weight of bagasse: 17.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 7.

TABLE 3

| | Biomass slurry concentration (w/v %) | Saccharification ratio (%) |
|---|---|---|
| Experimental Example 1 | 2 | 88 |
| Experimental Example 2 | 10 | 88.5 |
| Experimental Example 3 | 15 | 88 |
| Experimental Example 4 | 20 | 87.5 |
| Experimental Example 5 | 25 | 85.5 |
| Experimental Example 6 | 30 | 81 |
| Experimental Example 7 | 33 | 73 |
| Experimental Example 8 | 35 | 64 |

It was found from the results in Table 3 and FIG. 7 that when the biomass slurry concentration was more than 30 w/v %, the saccharification ratio of bagasse considerably decreased.

Experimental Example 9

A slurry containing bagasse was prepared by dispersing 1 g-dry of steam-exploded bagasse in 50 mL of a sugarcane juice (sucrose)-containing aqueous solution. The content (biomass slurry concentration) of the bagasse in the prepared slurry was 2 w/v %. The concentration (initial sucrose concentration) of the sugarcane juice (sucrose) contained in the slurry was adjusted to 140 g/L.

Subsequently, the bagasse contained in the biomass slurry was degraded using cellulase under the following conditions.

Weight of bagasse: 1 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The saccharification ratio of bagasse was assumed to be 100% when the entire cellulose contained in the bagasse was degraded into glucose. The saccharification ratio of cellulose was calculated from the amount of glucose produced.

Figure 8:
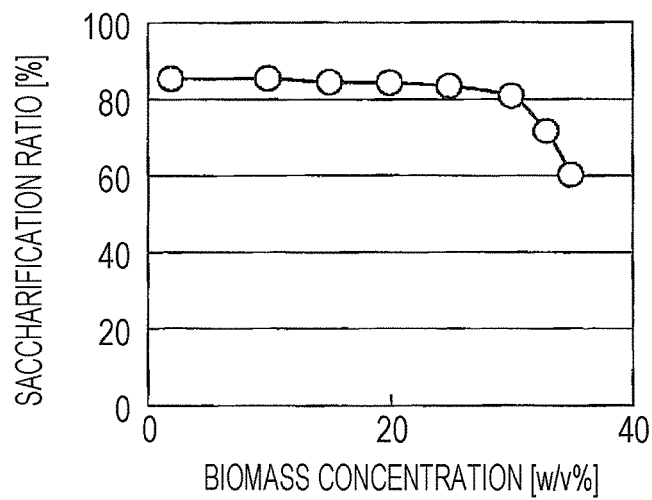
FIG. 8 is a graph illustrating the relationship between the saccharification ratio of biomass and the biomass concentration in Experimental Examples 9 to 16.

The results are shown in Table 4 and FIG. 8.

Experimental Example 10

A slurry containing bagasse was prepared by dispersing 5 g-dry of steam-exploded bagasse in 50 mL of a sugarcane juice (sucrose)-containing aqueous solution. The content (biomass slurry concentration) of the bagasse in the prepared slurry was 10 w/v %. The concentration (initial sucrose concentration) of the sugarcane juice (sucrose) contained in the slurry was adjusted to 105 g/L.

Subsequently, the bagasse contained in the biomass slurry was degraded using cellulase under the following conditions.

Weight of bagasse: 5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 4 and FIG. 8.

Experimental Example 11

A slurry containing bagasse was prepared by dispersing 7.5 g-dry of steam-exploded bagasse in 50 mL of a sugarcane juice (sucrose)-containing aqueous solution. The content (biomass slurry concentration) of the bagasse in the prepared slurry was 15 w/v %. The concentration (initial sucrose concentration) of the sugarcane juice (sucrose) contained in the slurry was adjusted to 85 g/L.

Subsequently, the bagasse contained in the biomass slurry was degraded using cellulase under the following conditions.

Weight of bagasse: 7.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 4 and FIG. 8.

Experimental Example 12

A slurry containing bagasse was prepared by dispersing 10 g-dry of steam-exploded bagasse in 50 mL of a sugarcane juice (sucrose)-containing aqueous solution. The content (biomass slurry concentration) of the bagasse in the prepared slurry was 20 w/v %. The concentration (initial sucrose concentration) of the sugarcane juice (sucrose) contained in the slurry was adjusted to 65 g/L.

Subsequently, the bagasse contained in the biomass slurry was degraded using cellulase under the following conditions.

Weight of bagasse: 10 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 4 and FIG. 8.

Experimental Example 13

A slurry containing bagasse was prepared by dispersing 12.5 g-dry of steam-exploded bagasse in 50 mL of a sugarcane juice (sucrose)-containing aqueous solution. The content (biomass slurry concentration) of the bagasse in the prepared slurry was 25 w/v %. The concentration (initial sucrose concentration) of the sugarcane juice (sucrose) contained in the slurry was adjusted to 40 g/L.

Subsequently, the bagasse contained in the biomass slurry was degraded using cellulase under the following conditions.

Weight of bagasse: 12.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 4 and FIG. 8.

Experimental Example 14

A slurry containing bagasse was prepared by dispersing 15 g-dry of steam-exploded bagasse in 50 mL of a sugarcane juice (sucrose)-containing aqueous solution. The content (biomass slurry concentration) of the bagasse in the prepared slurry was 30 w/v %. The concentration (initial sucrose concentration) of the sugarcane juice (sucrose) contained in the slurry was adjusted to 25 g/L.

Subsequently, the bagasse contained in the biomass slurry was degraded using cellulase under the following conditions.

Weight of bagasse: 15 g-dry
Amount of cellulase added: 2 mg/g-substrate
Amount of solution: 50 mL
Temperature: 50° C. pH: 5

The relationship between the bagasse content in the slurry containing bagasse and the proportion (saccharification ratio) at which the bagasse was degraded into glucose was investigated. The results are shown in Table 4 and FIG. 8.

Experimental Example 15

A slurry containing bagasse was prepared by dispersing 16.5 g-dry of steam-exploded bagasse in 50 mL of a sugarcane juice (sucrose)-containing aqueous solution. The content (biomass slurry concentration) of the bagasse in the prepared slurry was 33 w/v %. The concentration (initial sucrose concentration) of the sugarcane juice (sucrose) contained in the slurry was adjusted to 30 g/L.

Subsequently, the bagasse contained in the biomass slurry was degraded using cellulase under the following conditions.

Weight of bagasse: 16.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 3 and FIG. 8.

Experimental Example 16

A slurry containing bagasse was prepared by dispersing 17.5 g-dry of steam-exploded bagasse in 50 mL of a sugarcane juice (sucrose)-containing aqueous solution. The content (biomass slurry concentration) of the bagasse in the prepared slurry was 35 w/v %. The concentration (initial sucrose concentration) of the sugarcane juice (sucrose) contained in the slurry was adjusted to 40 g/L.

Subsequently, the bagasse contained in the biomass slurry was degraded using cellulase under the following conditions.

Weight of bagasse: 17.5 g-dry
Amount of cellulase added: 2 mg/g-substrate
Amount of solution: 50 mL
Temperature: 50° C.
pH: 5

The relationship between the bagasse content in the slurry containing bagasse and the proportion (saccharification ratio) at which the bagasse was degraded into glucose was investigated. The results are shown in Table 4 and FIG. 8.

TABLE 4

| | Biomass slurry concentration (w/v %) | Saccharification ratio (%) |
|---|---|---|
| Experimental Example 9 | 2 | 85 |
| Experimental Example 10 | 10 | 85 |
| Experimental Example 11 | 15 | 84.2 |
| Experimental Example 12 | 20 | 83.8 |
| Experimental Example 13 | 25 | 83 |
| Experimental Example 14 | 30 | 80.5 |
| Experimental Example 15 | 33 | 71 |
| Experimental Example 16 | 35 | 60 |

It was found from the results in Table 4 and FIG. 8 that when the biomass slurry concentration was more than 30 w/v %, the saccharification ratio of bagasse considerably decreased.

The invention claimed is:

1. A method for producing saccharides containing glucose as a main component, the method comprising:
   a) a step of preparing a slurry by adding an aqueous solution containing a sugar or a sugar solution to biomass so that the slurry has a biomass content of 10 to 30 w/v %; and
   b) a step of adding at least one of an enzyme that degrades cellulose and an enzyme that degrades hemicellulose to the slurry containing the biomass to degrade at least one of cellulose and hemicellulose contained in the biomass, thereby producing saccharides containing glucose as a main component,
   wherein in the step of preparing the slurry, when a content of the at least one of cellulose and hemicellulose in the slurry is assumed to be X (w/v %), an initial sugar concentration of the slurry is lower than a sugar concentration Y (g/L) represented by relation (1) below, $$Y = -7.7931X + 180 \qquad (1)$$

wherein, in the relation (1), X=W×C/100, where W represents a biomass slurry concentration (w/v %) and C represents a proportion (wt %) of the cellulose and the hemicellulose contained in the biomass.

2. The method for producing saccharides according to claim 1, wherein the sugar is glucose or sucrose.

3. The method for producing saccharides according to claim 1, wherein the sugar solution is an enzymatically saccharified solution or a solution containing a sugarcane juice.

4. The method for producing saccharides according to claim 1, wherein an adsorption inhibitor for inhibiting adsorption of an enzyme onto lignin contained in the biomass is added to the slurry.

* * * * *